United States Patent [19]

Jenkins et al.

[11] Patent Number: 5,380,542

[45] Date of Patent: * Jan. 10, 1995

[54] DIETARY FIBER COMPOSITIONS FOR USE IN FOODS

[75] Inventors: Ronald K. Jenkins; James L. Wild, both of Washington, Pa.

[73] Assignee: Rhone-Poulenc Specialties Chemical Co., Cranbury, N.J.

[*] Notice: The portion of the term of this patent subsequent to Mar. 15, 2011 has been disclaimed.

[21] Appl. No.: 73,358

[22] Filed: Jun. 11, 1993

Related U.S. Application Data

[63] Continuation-in-part of Ser. No. 901,331, Jun. 19, 1992, and a continuation-in-part of Ser. No. 901,464, Jun. 19, 1992.

[51] Int. Cl.$^6$ .................. A23L 1/0522; A23L 1/105; A23L 1/317
[52] U.S. Cl. ...................................... 426/573; 426/21; 426/28; 426/31; 426/579; 426/641; 426/644; 426/646
[58] Field of Search ................. 426/573, 646, 579, 21, 426/28, 31, 577, 804, 641, 644

[56] References Cited

U.S. PATENT DOCUMENTS

| | | |
|---|---|---|
| 3,754,925 | 8/1973 | Kimura et al. . |
| 4,284,722 | 8/1981 | Tamuri et al. ............... 435/94 |
| 4,348,420 | 9/1982 | Lynch et al. ............... 426/272 |
| 4,427,704 | 1/1984 | Cheney et al. . |
| 4,493,893 | 1/1985 | Mielenz et al. ............ 435/172.3 |
| 4,582,714 | 4/1986 | Ford et al. . |
| 4,647,470 | 3/1987 | Sanderson et al. . |
| 4,676,976 | 6/1987 | Toba et al. . |
| 4,724,208 | 2/1988 | Brewer et al. ............... 435/188 |
| 4,746,528 | 5/1988 | Prest et al. . |
| 4,894,250 | 1/1990 | Musson et al. . |
| 4,996,063 | 2/1991 | Inglett . |
| 5,011,701 | 4/1991 | Baer et al. . |
| 5,082,673 | 1/1992 | Inglett . |
| 5,192,569 | 3/1993 | McGinley et al. . |

OTHER PUBLICATIONS

Oatrim: New Maltodextrin Fat Substitute G. E. Inglett and S. B. Grisamore Jun. 1991.
Ift 1991 Dallas Carbohydrate Symposium, Application of Starched Based Fat Replacers: W. C. Yackel & C. L. Cox.
Development of Low-Fat Beef Patties with Added Dietary Fibers Webb Technical Group, for National Live Stock and Meat Board-Nov. 20, 1990.
Oatrim: Fat Reducer, Cholesterol Fighter. Dean D. Duxbury, Associate Editor, Food Processing, Aug. 1990.
Shemberg Carrageenan Brochure (undated).
Where's The Fat? Latest Ground Beef in 96% Free of it. Richard Gibson, Wall Street Journal, Oct. 3, 1991.
No One Fat Replacer Does It All. National Starch and Chemical Company Food Products Division Brochure (undated).
Oat Trim Update Given by U.S.D.A. at Oatrim Conference on May 18, 1990.
Food Additives. Ann M. Thayer, Chemical and Engineering News, Jun. 15, 1992.
Use of Specialty Food Addives to Continue to Grow. Ann M. Thayer, Chemical and Engineering News, Jun. 3, 1991.

*Primary Examiner*—Donald E. Czaja
*Assistant Examiner*—Mary S. Mims
*Attorney, Agent, or Firm*—Paul J. Juettner

[57] ABSTRACT

A cereal or grain hydrolysate-containing composition which is derived from the enzymatic, e.g., amylase, hydrolysis of cereal or grain in combination with a hydrocolloid, preferably carrageenan or a blend of xanthan gum and locust bean gum, can be effectively used as a fat mimic in preparing low fat comminuted meat products. Thermo-irreversible gels useful for providing non-fat fat mimics can also be prepared in accordance with the invention. In addition to amylase, the enzyme used for the hydrolysis of the cereal/grain substrate can be selected from the group consisting of amyloglucosidases ($\alpha$-1,4- glucan glucohydrolase), cellulases ($\beta$-1,4-glucanohydrolase), pullulanases (pullulane 6-glucanohydrolase), cyclodextrine glycosyltransferase ($\alpha$-1,4-glucan-4-glycosyltransferase), proteases and mixtures thereof.

55 Claims, No Drawings

DIETARY FIBER COMPOSITIONS FOR USE IN FOODS

CROSS-REFERENCE TO RELATED APPLICATIONS

The present application is a continuation-in-part of copending application Ser. Nos. 07/901,331 and 07/901,464, both filed Jun. 19, 1992.

BACKGROUND OF THE INVENTION

The present invention relates to the provision of dietary fiber compositions as well as thermo-irreversible gel particles for use in foods.

Recently, there has been an extensive emphasis on diet with the goal of reducing caloric and cholesterol intake. One of the major means of accomplishing this goal is the reduction of the intake of fat. Numerous fat mimic products are known and many are available commercially. One such product is an oat based extract patented under U.S. Pat. Nos. 4,996,063 and 5,082,673 issued to G. Inglett and identified as Oatrim. This product is the solids portion of the soluble fraction that remains after the partial hydrolysis of oat flour with α-amylase enzyme. The product has an elevated content of B-glucan. In addition to acting as a fat mimic, the product also has the benefit of the known ability of oat soluble fiber and $\beta$-glucan to reduce the cholesterol levels in the blood.

While Oatrim has been used in various food systems as a fat mimic or replacer, it has various limitations relative to the area of use. In particular, Oatrim has been added to various ground meat products in order to prepare a reduced fat meat patty or sausage, e.g., frankfurter. However, Oatrim by itself in meat products, while providing cook yields, provides a meat product that exhibits a weak or mushy texture.

In certain processed meat products, definitive fat particles or fat islands are observable within the meat product. While many fat mimics provide the slippery characteristic of fat, most do not lend themselves to the formation of fat mimic particles which are stable at the heating or cooking temperatures of the meat product. Sausages such as kielbasa, pepperoni and salami rely on the tat particles for appearance, taste and mouth feel. These tat particles are recognized by the consumer as an essential part of the product. In order to provide a fat reduced sausage of this type, it will be necessary to substitute the fat particles with non-fat particles which can provide the taste and mouth feel of the original product and which can withstand the processing temperatures and cooking conditions (smoking, boiling, baking, and barbecuing) applied to these products. Oatrim as presently constituted cannot be used effectively to provide fat mimic particles satisfying these characteristics and conditions.

It has been discovered that Oatrim compositions can be prepared which provide good yield and good water-holding capacity while providing a fat reduced product with the visual, taste and mouth feel properties characteristic of a full fat meat product. It has further been discovered that thermo-irreversible gels can be prepared using Oatrim as the base which withstand the heating and cooking needed to provide that type of product while providing the visual, taste and mouth feel characteristics desired in a fat mimic particle for meat products.

SUMMARY OF THE INVENTION

In accordance with the invention, water soluble and insoluble dietary fiber-containing compositions which are based on cereal hydrolysates are provided which are characterized by good cook yields in comminuted meats as well as organoleptic characteristics comparable to the full fat product and also the benefits of $\beta$-glucan. The water soluble dietary fiber compositions can also be made into thermoirreversible gels according to the invention. These compositions can be mixed with food to effect a replacement of fat or other ingredients or act as a filler or flavor carrier or decoration. Particularly, the compositions can be used as fat mimics in combination with comminuted meats in such products as sausages.

The claimed compositions are achieved by blending soluble and/or insoluble dietary fiber compositions, also described as cereal hydrolysates, as defined hereinafter with a hydrocolloid as defined herein. Thermo-irreversible gels can be achieved by blending gelatinized cereal hydrolysates with a hydrated hydrocolloid as described herein.

DETAILED DESCRIPTION OF THE INVENTION

As used herein, the term "Oatrim" is intended to specifically refer to the solids recovered from the water soluble fraction after separating the soluble fraction from the insoluble fraction by partial hydrolysis of oat flour as defined herein.

Broadly, the term "oat hydrolysate" is intended to cover a) the solids from the soluble fraction prepared from oats as defined above, b) the insoluble fraction as defined above and c) the total solids obtained after the hydrolysis of the cereal forming the soluble and insoluble fraction without isolation of the fractions.

The term "cereal hydrolysate" is intended to cover the same products as listed under the oat hydrolysate but prepared using the cereals as listed hereinafter.

The hydrolysate used in the invention, e.g., the soluble dietary fiber material, can be formed using the process of U.S. Pat. Nos. 4,996,063 and 5,082,673, the disclosures of which are incorporated herein by reference.

The term "thermo-irreversible gel" as used herein is intended to mean a gel which substantially retains its shape and integrity in the system in which it is used after heating the system to a temperature of 71° C. (160° F.) for 15 minutes.

Suitable substrates contemplated for use in preparing the hydrolysates used in the invention include cereal flours, milled cereal brans, cereal starches, tuber starches, and blends thereof. Of particular interest are the whole flours of barley, oats, wheat, corn, rice, rye, triticale, and milo, as well as the flours prepared from bran or other fractions of the milled grain. Preferably, the substrate is whole oat flour.

The substrate is slurried in a sufficient amount of water to give a concentration in the range of about 10–40% by weight. The water can contain a suitable calcium content in an amount sufficient to stabilize the subsequently added enzyme, e.g., α-amylase, such as about 25–50 part per million (ppm) of calcium. The slurried substrate may be gelatinized prior to enzymatic treatment, using any method known in the art such as heating. The pH of the ungelatinized slurry or the gelatinized dispersion can be adjusted to about 5.5–7.5, preferably about 6.0, with appropriate acid or base addition, i.e., sodium hydroxide or other alkali. Enzyme concentration of approximately 0.4–5 g/kg (dry weight) of substrate can be used.

It is advantageous to use thermostable α-amylase referred to as 1.4-α-D-glucan glucanohydrolases and having the essential enzymatic characteristics of those produced by the Bacillus stearothermophilus strains ATCC Nos. 31,195; 31,196; 31,197; 31,198; 31,199; and 31,783. These strains are described in U.S. Pat. No. 4,284,722 which is incorporated herein by reference. Other sources of this enzyme include organisms as B. subtilis which have been genetically modified to express the thermostable α-amylase of B. stearothermophilus as described in U.S. Pat. No. 4,493,893 incorporated herein by reference. These enzymes are available commercially under the name "G-zyme G995" (formerly called "Enzyme Thermolase"; Enzyme Development Div., Biddle Sawyer Corp., New York, N.Y.)

Other suitable α-amylases are those produced by B. licheniformis var. as described in U.S. Pat. Nos. 4,717,662 and 4,724,208, herein incorporated by reference. These enzymes are available commercially under the name "Taka-Thermal-340" (formerly called "Taka-lite" Solvay Enzyme Products, Inc., Elkart, Ind.). Of course, any α-amylase which is useful in the thinning of the starch is contemplated for use therein.

In addition to tile alpha amylase, the process of preparing Oatrim can be accomplished using enzymes selected from the group consisting of amyloglucosidases (α- 1,4 -glucan glucohydrolase), cellulases (β-1,4 glucan glucanohydrolase), pullulanases (pullulane 6 - glucanohydrolase), cyclodextrine glycosyltransferase (α-1,4-glucan-4-glycosyltransferase), proteases, and their combinations.

Surprisingly, tile aforementioned enzymes have proven to be active vis-a-vis the grain flours. Their enzymatic action leads to the formation of the corresponding water soluble or water dispersible extracts, which have proven to be particularly interesting as food additives.

Amyloglucosidase is an exo-amylase produced by fermentation of an Aspergillus Niger culture. The enzyme is not specific to α-1,4 bonds and also hydrolyzes α-1,6 bonds of starch.

The cellulase is a cellulolytic, fungal enzyme derived from the Trichoderma longibrachatium culture. It can hydrolyze the α-1,4 bonds of xylene and arabinoxylane just as the beta-1,4- glycosidic bonds of the βglucan and cellulase.

Pullulanase is produced by klebsiella planticola and hydrolyses α-1,6 glucosidic bonds of pullulane and amylopectine.

The proteases arc, produced by a Bacillus licheniformis coating, the principal enzymatic constituent of which is the reactant that attacks the peptide bonds, and in lesser measure, the ester bonds.

The conditions of enzyme treatment, including the enzyme concentration and the time and temperature of reaction, are selected to achieve liquefaction of the starch in the substrate. When using a thermostable α-amylase, a preferred treatment temperature is in the range of 70°–100° C., preferably about 95° C. At these temperatures, gelatinization of the starch in the substrate occurs concurrently with the hydrolysis. The duration of the treatment at the desired conversion temperature depends on the desired product properties and will generally range from about 2–60 min. Temperatures as low as 55°–60° C. can be used depending on the activation temperature of the enzyme.

After completion of the enzymatic hydrolysis, the enzyme is inactivated, such as by passing the mixture through a steam injection pressure cooker at a temperature of about 125°–140° C. Alternatively, the enzyme may be inactivated by acidification (pH 3.5–4.0) at 95° C. for about 10 min. A combination of these methods can also be used. Optional neutralization with alkali increases the salt concentration of the product and this could be less desirable. A natural pH product can be made by avoiding the acid enzyme inactivation step and relying solely on heat inactivation. After the enzyme has been inactivated, the soluble fraction comprising the soluble dietary fiber and the maltodextrins (maltooligosaccharides) is separated from the insoluble residue by any appropriate means such as by centrifugation of the hydrolysates. In a preferred embodiment of the invention, temperatures during centrifugation are maintained less than 70° C., and most preferably within the range of 5°–50° C. Under these conditions of separation, the levels of lipids and proteins in the dietary fiber products are significantly reduced. Water is then removed from the soluble fraction by any of a variety of conventional techniques, whereby the products of this invention comprising the dietary fiber and maltodextrins are recovered. The maltodextrins produced by the process of the invention have a D.E. of 20 or less. These maltodextrins are substantially water soluble at elevated temperatures (e.g., 70°–100° C.)

The soluble dietary fiber recovered from the centrifugate is principally in the form of β-glucans and pentosans, Of course the relative amount of each fiber type varies with the species of substrate. Oat and barley substrates yield mostly the β-glucans, whereas wheat, rice, and corn yield the pentosans.

The insoluble fraction recovered from the centrifuge can also be used though not as effectively as the soluble dietary fiber. If desired, the product from the hydrolysis step can be dried to recover both the soluble and insoluble solids. The benefit derived by this procedure is the use of all the components without loss or expense in disposing of the insoluble fraction.

Representative Method of Preparing Soluble Oat Fiber in accordance with Example 10 of U.S. Pat No. 5,082,673

Six kilograms of oat flour can be slurried in 18 liters of water containing 25 ppm of calcium. The pH of the slurry was 5.75. After gelatinization by passage of the mixture through a steam injection cooker, the slurry can be collected in a 30 gallon (113.5 liter) steam-heated cooker. Alpha amylase can then be added to the slurry in an amount sufficient to provide 1 unit per gram of oat flour. After 5 minutes of stirring at 80°–90° C., the enzyme can be inactivated by passing the slurry through a steam injection cooker. The warm slurry can be centrifuged at 15,000 rpm by a large "Sharples" centrifuge to separate the soluble and insoluble components. The products can be dried separately on hot rolls. The oligomer composition can be 98% DP 9 and larger.

The hydrocolloids for use in the invention include carrageenan (kappa or iota) or a mixture of xantham and locust bean gum. Preferably, the hydrocolloid is carrageenan or a mixture of xanthan and locust bean gum. Effective ratios of xanthan to locust bean depend on use area (e.g. 4:1 to 1:4), preferably 1:1.

The hydrocolloids can be used in dry admixture with the hydrolysate or pre-gelled with the soluble dietary fiber composition by blending the water soluble dietary fiber composition and the hydrocolloid in water, preferably hot (75°-100° C.) water until the substrate is swollen and the gum is dissolved and well mixed. The gels are prepared by blending the water soluble dietary fibers and the hydrocolloid in hot (75°-100° C.) water until dissolved and well mixed. After cooling, such as in a refrigeration over night, the gel is set. The gel is usually comminuted to small pieces such as within the range of from about 0.1 cm to about 1.30 cm. The gel can be stored in a cool place until needed for use to prevent bacteriological degradation. The gel can be prepared with coloring, flavors, preservatives, protein enhancers, fillers and the like. The gel can be used chopped or in shaped particles.

The cereal hydrolysate is used in a dry solids ratio to the hydrocolloid of from about 80–88 parts hydrolysate to from about 20 to about 12 hydrocolloid, preferably from about 88 to about 86 parts to from about 18 to about 14 parts and more preferably from about 83 to about 85 parts to from about 17 to about 15 parts. Most preferably, the cereal hydrolysate is used in an amount of 84 parts hydrolysate to 16 parts hydrocolloid. The blend of xanthan gum and locust bean gum would be considered a hydrocolloid for these ratios. The gel is preferably prepared in a 1:3 weight basis ratio of solids to water.

The gel or the dry blend is added to the comminuted meat in an amount as needed to provide the effect needed. In general, the gel can be used in an amount ranging from about 4 to about 30%. The gel can be used as a fat mimic to replace the fat on a ratio of 1:1 depending on the moisture content in the gel.

As used herein, comminuted meat is intended to cover meat muscle which has been interrupted from its natural form such as by cutting, shredding, chopping, grinding, emulsifying and the like. The comminuted meat pieces preferably have a size of less than 2.5 centimeters (1 inch) and more preferably less than 0.6 centimeters (0.25 inch). Appropriate particle sizes for products such as patties and sausages are well known to the skilled artisan.

The comminuted meat may be derived from any usual meat source using any conventional recipe [such as from bovine (cow, bull, steer, calf), sheep (lamb and mutton), swine (pigs, hogs), wild game (elk, deer) and fowl (chicken, turkey, duck, goose)] and conventional preparation techniques such as disclosed in "Sausage and Processed Meats Manufacturing, Robert E. Rust, AMI Center for Continuing Education, American Meat Institute (1977), which is incorporated herein by reference.

The comminuted meat can include conventional ingredients such as curing agents and preservatives, spices, and flavor accentuators, fillers, coloring, and the like. These can be illustrated by alkali metal chlorides, nitrites, nitrates, phosphates (pyro and poly), sorbates, benzoates, erythorbates, citrates and citric acid, sugar and sugar derivatives, cereal flour and cereal derivatives, spices and spice extracts, oleo resins, seasonings, flavors, curing adjuncts such as glutamic acid and GDL, fats, oils, modified fats and oils, solvents such as water, alcohol or glycerin, vitamins, amino acids, proteins (natural, hydrolyzed, modified, isolated), flavor enhancers such as MSG or soy sauce, smoke flavorings, coloring agents such as paprika, tomato pumice, beet extract, artificial colors as desired.

The comminuted meat products can be in the form of patties, sausage, cooked and fermented sausage (salami and pepperoni), frankfurters (hot dogs) and the like products made from chopped meat, spices, preservation agents (nitrites, erythorbates, phosphates) and the like either formed or in casings.

The following examples are presented only to further illustrate the invention and are not inserted to limit the scope of the invention which is defined by the claims.

All percentages are by weight unless otherwise stated.

EXAMPLE 1

Materials and Formulations

The Oatrim used in the following example was prepared by admixing at room temperature sufficient whole oat flour with water containing calcium to provide a slurry of about 25 % solids by weight. The pH of the slurry is 6.2. Taka-therm enzyme in the amount equivalent to 0.7 grams per kilogram of total solids was added. The enzymatic hydrolysis was allowed to proceed at 92°-95° C. for a retention time of 1.5-2 minutes. The pH was then adjusted to pH 4 with phosphoric acid and heated to 130° C. for six minutes in order inactivate the enzyme. The pH was then adjusted to 5.5 with caustic and the material was centrifuged to separate the insoluble solids from the mother liquor. The mother liquor was dried in a drum dryer to provide the Oatrim product which had a pH of 5.3, a viscosity of 58 centipoise (5% solution using spindle #3) and a moisture content of 6.7%.

Of the fat mimics used in this Example, three dry blends were also prepared:

| 1. Mimic-III (Dry) | |
|---|---|
| a. Oatrim | 84% |
| b. Kappa Carrageenan | 16% |
| 2. Mimic-I (Dry) | |
| a. Oatrim | 84% |
| b. Iota Carrageenan | 16% |
| 3. Mimic III (Dry) | |
| a. Oatrim | 84% |
| b. Xanthan | 8% |
| c. Locust Bean Gum | 8% |

Three preformed gels were also prepared:

| 1. & 2. Mimic-III [Kappa] (Gel) or Mimic-I [Iota] (Gel) | |
|---|---|
| a. Oatrim | 21% |
| b. Kappa Carrageenan | 4% |
| or | |
| Iota Carrageenan | |
| c. Water | 75% |
| 3. Mimic II [Oatrim/Xanthan Gum/Locust Bean Gum] (Gel) | |
| a. Oatrim | 21% |
| b. Xanthan Gum | 2% |
| c. Locust Bean Gum | 2% |
| d. Water | 75% |

PROCESS FOR PREPARING GELS

After boiling the water, weighing and mixing the dry ingredients, and calibrating a food processor bowl (Cuisinart) to 375 grams of liquid, the boiling water was poured into the food processor bowl up to the previously calibrated 375 gram level. The temperature immediately after pouring was recorded, specification is 90° C. or higher. With the food processor blades in operation, the dry ingredients were rapidly blended into the water, mixing for one minute on low speed. Discontinue mixing or chopping once the mixture has cooled to 70° C. The resultant slurry/gel was removed to a sealable container (beaker) and placed in cooler 0° C. –3.3° C. (32°–38° F.) overnight to set the gel.

MEAT MIXTURE COMPOSITION

With the exception of the 30% fat control, the base formulation contained the following:

| | |
|---|---|
| Pork Trim | 21.63% |
| Beef Round | 3.14% |
| Pork Picnic | 38.25% |
| Water | (32.50%-DryFat Replacer) + 10% Added Water |
| Fat Mimic | See Table I. |
| Spice (Includes Salt) | 4.40% |
| Sodium Erythorbate | (0.06%) |
| Sodium Nitrite | (0.02%) |

Each low-fat formulation was prepared to contain 239.5 bind units (U. Georgia, College of Agriculture) and 9.5 % fat content as per the guidelines for a low-fat frankfurter formulation. Treatment addition levels of the various fat mimic ingredients are listed in Table I.

The 30% fat control contained:

| | |
|---|---|
| Pork Trim | 11.52% |
| Pork back fat | 24.00% |
| Beef Round | 11.00% |
| Pork Picnic | 34.00% |
| Water | 15.00% |
| Spice (+ salt) | 4.40% |
| Sodium Erythorbate | 0.067% |
| Sodium Nitrite | 0.02% |

MEAT MIXTURE PREPARATION

For each treatment, separate meat blocks were prepared according to the base formulation previously described. Prior to chopping in a food processor (Cuisinart), the treatment formulation was blended using a Hobart planetary mixer according to the following procedures:

1. Meat block components were mixed for 30 seconds at slow (#1) speed.
2. The spice blend including the salt and sodium erythorbate were added and mixed for an additional 30 seconds at the #1 setting.
3. Ice water and the dry fat replacer ingredients (if applicable) were added and mixed for 60 seconds at the #1 speed setting.
4. Pre-dissolved sodium nitrite was added and mixed for a final 30 seconds.
5. From each of the mixed meat blocks, five 1000 gram units were removed and assigned to each of five chopping times at 0, 1, 2, 3, 4, and 5 minutes.
6. In the 4 treatments using the preformed gel, only water was added in Step 3. The gels, pre-chopped by hand (knife), were added (140 grams) to an 860 gram mixed meat block immediately prior to food processor chopping in Step 7.
7. The 1000 gram units were then chopped for 0, 1, 2, 3 or 4 minutes using a food processor (Cuisinart Model DLC-7). Temperatures of the mixture following chopping were recorded. The sides of the food processor bowl were scraped every minute to insure a more homogeneous mixture.
8. Each treatment was then placed into two aluminum loaf pans. A vacuum was not drawn to eliminate air pockets as the formulations were very fluid.
9. Each loaf pan was weighed and then crimp covered with aluminum foil. All loaves were then kept at 1.1 ° C. (34° F.) overnight prior to smokehouse cooking.

COOKING PROCEDURE

Following the overnight chilling, the loaves were smokehouse cooked 2.5 hours at a wet bulb/dry bulb temperature of 76.6°/60° C. (170°/140° F.) until an internal temperature of 71 ° C. (160° F.) was reached and maintained for at least 15 minutes. The loaves were kept in an unheated smokehouse for 1.5 hours after which each loaf was weighed and the cook purge drawn off and volumetrically measured. Each loaf was then placed into a plastic pouch and held at 1.1° C. (34° F.) until needed for organoleptic appraisal.

The loaves were stored at 1.1° C.(34° F.) for 5 days prior to sensory evaluation. The 4 minute chop series of the treatment samples were then evaluated for texture, flavor and visual quality.

TABLE I

| AVERAGE COOK YIELD (%) BY CHOP TIME IN MINUTES | | | | | |
|---|---|---|---|---|---|
| | 0 | 1 | 2 | 3 | 4 |
| Mimic-III (Dry) 3.5% | 68.70 | 86.50 | 89.30 | 89.70 | 88.40 |
| Mimic-III (Gel) 14% | 84.80 | 93.80 | 94.80 | 94.40 | 92.90 |
| Mimic-I (Dry) 2.5% | 67.30 | 84.10 | 85.50 | 86.20 | 83.30 |
| Mimic-I (Gel) 14% | 85.10 | 92.10 | 90.03 | 86.10 | 84.70 |
| Mimic-I (Dry) 3.5% | 69.30 | 83.90 | 86.30 | 87.90 | 86.70 |
| Mimic-II (Dry) 3.5% | — | 95.00 | 93.40 | 94.20 | 94.60 |
| Mimic-II (Gel) 14% | 86.10 | 96.00 | 95.90 | 96.10 | 95.60 |
| CONTROL SAMPLES | | | | | |
| Control (10% Fat) | 67.77 | 81.19 | 85.09 | 86.81 | 85.67 |
| Control (30% Fat) | 82.91 | 91.18 | 81.22 | 76.37 | 70.64 |
| Oatrim (3.5%) | 66.21 | 76.59 | 79.69 | 80.63 | 77.79 |
| Oatrim (2.5%) | 63.10 | 75.60 | 81.60 | 81.30 | 80.60 |
| Rice-trin* (3.5%) | 67.60 | 74.40 | 76.40 | 77.20 | 76.20 |
| Carrageenan-Kappa (0.5%) | | | | | |
| Source A | 80.00 | 90.2 | 92.60 | 93.70 | 94.00 |
| Source B | 82.00 | 92.10 | 93.5 | 95.00 | 93.80 |
| Oat Bran (3.5%) | 84.80 | 93.30 | 94.10 | 94.40 | 94.20 |

*Rice-trin is a commercially available fat mimic.

RESULTS

Cook Yields

Cook yields by formulation and chop time are summarized in Table I. With the majority of the formulations exhibiting maximum cook yields following 3 minutes of chop time, a ranking of yields was prepared and presented as table 2. Of the fat mimics evaluated, the highest cook yields and the greatest stability to over chop stress (no yield loss over length of chop) were attained with the dry and gel forms of Mimic-II and Mimic-III blends.

Gels of Mimic-II and Mimic-III provided higher cook yields than the dry counterparts. The differences between the two forms of Mimic-III were pronounced whereas the differences between the two versions of Mimic-II were small. The yields for Mimic-I were lower and could indicate that this gel form is not resistant to high stress.

ORGANOLEPTIC and VISUAL APPRAISAL
Loaf- 10% Frankfurter mixture

Informal organoleptic evaluations were conducted on the 4 minute chop series.

Texture

The texture of the 30% fat control appeared dry, firm and chewy as compared to the softer, smoother texture of the low-tat control. Of the low-tat formulations, the low-fat control, both carrageenan treatments, the oat bran and the dry application of Mimic-II and Mimic-I provided the firmest products. Single use of Oatrim and Rice-trin treatments provided meat products which appeared dry and mealy.

Flavor

With the exception of the a slight bitterness detected with the Source-A carrageenan, the flavor of the various tat replacers was considered acceptable. Primary differences between treatments appeared to be based on the intensities of spices, sugar and smoke flavor perception. Those treatments containing either Mimic -I or Mimic-II appeared to be sweeter than the other treatments.

Visual Appraisal

Many air pockets were present throughout the cooked products due to the inability of a vacuum treatment to lower the residual air. Except for Mimic-II and Mimic-III gel systems, the low fat loaves were similar in appearance. Small minute gel particles were visible in the Mimic-II and Mimic-III chop series. As such these gels are easily sheared and since the raw meat batters showed no evidence of such particles, it is concluded that the fine gel particles remaining following chopping continued to hydrate during the subsequent dwell and cook processes. With such additional hydration, the swollen gel particles thus appeared visible in the cooked matrix.

While, of the single ingredient systems, both kappa carrageenan and oat bran, provided the highest cook yields and chop stabilities, the gel and dry forms of Mimic-II and Mimic-III provided the highest cook yields and chop stabilities along with the benefits of the soluble dietary fiber product. This is in contrast to Oatrim only treatments which provided only a measure of chop stability, and cook yields were lower than that of the low-fat (10%) fat control.

With the possible exception of the Oatrim and Rice-trin formulations which appeared dry and mealy, none of the low-fat treatments exhibited a negative textural state. Flavors were acceptable for the products of the invention. The presence of small gel pockets within the Mimic-II and Mimic-III gel treated loaves was a negative visual effect that could possibly be avoided by better gel hydration or increased milling of the meat emulsion.

EXAMPLE 2

The Oatrim utilized in the following examples was prepared by admixing sufficient whole oat flour at room temperature with a pre-determined amount of calcium containing (100 ppm) water to provide a slurry of 20% solids by weight. Taka-therm enzyme was added to the slurry in an amount of 1.0 grams per kilogram of total solids diluted with 19.(, grams of water. The enzymatic hydrolysis was allowed to proceed at 90° C. for two minutes in a pressure cooker. The enzyme was inactivated by cooking in a pressure cooker at 131° C. The slurry was flashed to release excess vapor and odor. After removing the insoluble portion by centrifugation, the mother liquor was dried in a drum dryer. The product had a viscosity at a 5% solution of 88 centipoise (using spindle #3), pH of 6.29 and a moisture content of 3.9%.

BEEF PATTIES

Numerous evaluations have been performed comparing cook yields and organoleptic performance of reduced fat beef patties formulated to contain either an iota carrageenan or Mimic-I, (a 84:16 blend of Oatrim and iota carrageenan). To date, the results have shown the Mimic-I formulation [89.13% lean beef (6–9% fat), 2.0% Mimic-I 1, 8.5% water and 0.37% encapsulated salt] provided higher cook yields, better beef flavor release, softer texture and greater initial and sustained juiciness than a beef patty formulation using iota-carrageenan alone [89.13 beef (6–9% fat), 10% water, 0.5% iota carrageenan and 0.37% encapsulated salt]. Cook yield and organoleptic performance data from a recent evaluation are provided below in Table II.

TABLE II

COOK YIELDS AND ORGANOLEPTIC RESPONSES FOR REDUCED FAT BEEF PATTIES

| Treatment | Mean Cook Yield % (n = 8) | Organoleptic Means (n = 7) | | | |
|---|---|---|---|---|---|
| | | Texture | Juiciness | Flavor | Preference |
| Iota Carrageenan | 67.9 | 6.9 | 4.8 | 5.6 | 4.9 |
| Mimic-I | 72.2 | 5.6 | 6.5 | 6.7 | 6.9 |

Hedonic Scale 0–9, 9 being highest

EXAMPLE 3

PORK SAUSAGE PATTIES

Using a gel application of Mimic-I (75 parts water: 25 parts dry Mimic-I), reduced fat pork sausage patties were formulated to contain 87.38% lean pork (ca. 10% fat), 10.5% Mimic-I gel. 1.0% encapsulated salt and 1.12% spice/seasoning blend. The cook yield and organoleptic performance of this formulation was compared to that of a high fat (30%) control, a reduced fat (9%) control and a reduced fat Iota-carrageenan-containing product, formulations of which are set forth below in Table III.

TABLE III

| | Formulation Content: Pork Sausage Patties Ingredient Percentages | | | | | | | |
|---|---|---|---|---|---|---|---|---|
| Treatment | Lean Pork | Back Fat | Water | Carrageenan Iota | Mimic-I Gel | Encap. Salt | Spice Season | Fat Content |
| Low-fat control | 87.38 | — | 10.5 | — | — | 1.0 | 1.12 | 9% |

TABLE III-continued

| Treatment | Formulation Content: Pork Sausage Patties Ingredient Percentages | | | | | | | |
|---|---|---|---|---|---|---|---|---|
| | Lean Pork | Back Fat | Water | Carrageenan Iota | Mimic-I Gel | Encap. Salt | Spice Season | Fat Content |
| High fat control | 73.41 | 24.47 | — | — | — | 1.0 | 1.12 | 30% |
| Mimic I (gel) | 87.38 | — | — | — | 10.5 | 1.0 | 1.12 | 9% |
| Iota Carrageenan | 87.38 | — | 10.0 | 0.5 | — | 1.0 | 1.12 | 9% |

TABLE IV

Reduced Fat Pork Sausage Patties
Cook Yield and Organoleptic Responses

| Treatment | Grill Cook Yield % (6 min. @ 122° C). | Organoleptic Means | | | |
|---|---|---|---|---|---|
| | | Texture | Juiciness | Flavor | Preference |
| Low-fat control | 64.3 | 6.8 | 5.0 | 5.8 | 4.8 |
| High-fat control | 53.7 | 6.7 | 5.5 | 5.1 | 4.8 |
| Mimic-I Gel | 71.8 | 5.1 | 7.0 | 7.4 | 7.3 |
| Iota Carrageenan | 71.1 | 6.4 | 4.8 | 5.3 | 5.0 |

An ideal fat mimic or fat replacer ingredient system will provide a reduced fat product with organoleptic properties similar to that of the high fat standard. Based on the results provided above (Table IV), the use of the Mimic-I (gel) in a reduced fat pork sausage product provides cook yield and organoleptic performance equal or superior to that of the high fat standard.

EXAMPLE 4

To study the efficacy of using a firm thermally stable gel as a fat replacer in a course-cut sausage product, a fat reduced kielbasa was prepared containing a fat particle look-alike comprised of Mimic-Ill (gel). The gel, prepared using a Hobart planetary mixer (speed #2) and boiling water (mixed 1 minute), consisted of 75 parts water and 25 parts of dry Mimic-III (84 parts Oatrim and 16 parts kappa carrageenan). Formulations for the standard high fat (30%) kielbasa and a reduced fat (10%) version containing the Mimic-Ill (gel) are listed below in Table V.

TABLE V

| Treatment | Ingredient % | |
|---|---|---|
| | Hi Fat Control | Mimic-κ (gel) |
| Fresh Ham | 40.51 | 45.38 |
| Beef (90/10 trim) | 15.51 | 12.51 |
| Pork Back fat | 21.55 | 4.67 |
| Water | 17.5 | 20.0 |
| Mimic-III (gel) | — | 12.5 |
| Spice and Salt | 4.5 | 4.5 |
| Phosphate | 0.4 | 0.4 |
| Nitrite | 0.01 | 0.01 |
| Erythorbate | 0.03 | 0.03 |

The smokehouse cook yields for the high fat control and Mimic-III treatment were identical (79%). Although the kielbasa was not tested by a formal panel, at least a dozen staff members tasted the product in both a cooked, chilled and a reheated state. The remarks were consistent with the reduced tat Mimic-III product closely resembling the high fat control sample. The visible gel particles resembled the characteristic visible fat particles in the high fat standard product. The Mimic-Ill (gel) pieces provided a mouth feel similar to that of the fat particles in the high fat standard. The texture of the reduced tat product was slightly firmer but still considered highly acceptable.

The use of Mimic-III (gel) in pepperoni is currently being tested. Preliminary results indicate that the pepperoni has a desirable flavor texture and mouth feel. The simulated fat particles (i.e, Mimic-III (gel)) exhibited fat like characteristics during grinding and further processing (stuffing, etc.).

EXAMPLE 5

Frankfurters

Using the formulations outlined in Tables VI, both high fat (standard) and reduced-fat, frankfurters were prepared. The raw frankfurters were chopped to 15.5° C. after which the meat emulsions were stuffed into cellulose casings and smokehouse cooked to an internal temperature of 69° C. Cook yields are reported in Table VII:

TABLE VI

| Ingredients % (Grams) | Dry Ingredients - % - Low Fat Frankfurters | | | |
|---|---|---|---|---|
| | Mimic-II (10% Fat) | High Fat Control (30% Fat) | κCarrageenan (10% Fat) | Low Fat Control (10% Fat) |
| Salt | 2.10 | 2.10 | 2.10 | 2.10 |
| Sugar | 2.31 | 2.31 | 2.31 | 2.31 |
| Seasoning | 0.38 | 0.38 | 0.38 | 0.38 |
| CV-250 | 0.42 | 0.42 | 0.42 | 0.42 |
| Mustard | 0.84 | 0.84 | 0.84 | 0.84 |
| Corn Syrup Solids | 2.00 | 2.00 | 2.00 | 2.00 |
| Oatrim/K-Carrageenan | 2.94 | — | 0.50 | — |
| Xanthan | 0.28 | — | — | — |
| Locust Bean Gum | 0.28 | — | — | — |
| Sodium Nitrite | 0.01 | 0.01 | 0.01 | 0.01 |

TABLE VI-continued

| | Dry Ingredients - % - Low Fat Frankfurters | | | |
|---|---|---|---|---|
| Ingredients % (Grams) | Mimic-II (10% Fat) | High Fat Control (30% Fat) | κCarrageenan (10% Fat) | Low Fat Control (10% Fat) |
| Sodium Erythorbate | 0.03 | 0.03 | 0.03 | 0.03 |

TABLE VII

| | Frankfurter Cook Yields | |
|---|---|---|
| Treatment | Cook Yield % Batch | Adjusted Cook Yield (+ 10% Added Water) |
| 1. High Fat Control | 88.5 | 98.5 |
| 2. Kappa Carrageenan | 76.8 | 86.8 |
| 3. Mimic-11 ( ) | 79.8 | 89.8 |
| 4. Low Fat Control | 80.3 | 90.3 |

Although no normal taste panel evaluations were conducted on the products, many informal tastings were performed. The Mimic-II treatment was considered similar to the high fat control in flavor, texture, juiciness and color. Frankfurter skin thickness was considered excessive for the low-fat control and the kappa-carrageenan treatments. Although the frankfurter skin was thicker with the Mimic-II product as compared to the high fat control, the degree of increased thickness was not considered a negative attribute.

The properties of the frankfurters prepared in accordance with the invention and high fat control samples were considered very acceptable by many whereas the carrageenan frankfurter's texture was considered too soft and mushy.

The following examples relate to the use of enzymes other than α-amylase.

The enzymes used in the following examples are available commercially. These include the following enzymes:

AMG 300 L ®, (amyloglucosidase), Cellulase XL ®, Pulluzyme 750 ® (Pullulanase), Alcalase 2.4 L ®¢ Protease), Celluclast 1.5 L ®, CGtase and Ambazyme P 20 ®. Ambazyme is a commercial formulation combining amyloglucosidase and pullulanase.

The viscosities in the tables that follow were evaluated, except where otherwise noted, with the help of a Brookfield ®LVT with a n° 1 needle at 60 rpm.

EXAMPLE 6

Preparation of water soluble extracts from oat flour-a preferred method

Under agitation, blend oat flour into spring water containing 100 ppm of $Ca^{++}$to prepare an 18% slurry of flour in water. Meter in a sufficient amount of a cellulase enzyme, e.g., Celluclast 1.5L, at a rate of 1–1.2 g/kg flour. Heat the mixture in a jet cooker at 90° C. for 2 minutes followed by heating in a second jet cooker at 130° C. for 5–8 minutes. Cool the material from the second jet cooker in a flash tank and then centrifuge the resultant product to separate the solids from the liquids. The supernatant is separated and directed to a drum dryer/flaker to dry the product. The dried and flaked product is then reduced in size in a hammer mill and bagged.

EXAMPLE 7

Preparation of water soluble extracts from oat flour.

Under agitation, pour oat Hour into spring water containing 100 ppm of $Ca^{++}$. Adjust the pH of this prepared solution, if needed, to between 6.1 and 6.5 with phosphoric acid or soda. Heat this flour solution continuously at 20° C. in a jet cooker at an evaporation rate of 165 kg/h, and heat at 115° C. with a relative pressure of $2 \times 10^5$ Pa by vapor injection to achieve a contact time of 2 minutes. The treated solution is allowed to flow in a temperature regulated, vibrating reactor. Cool the solution to 55°–60° C. under agitation, while maintaining the volume at 50 liters to obtain an enzyme contact time in approximately 15 minutes. Sustain the enzyme in the reactor continuously by a volumetric pump, and depending on the enzyme used, fluidification will occur with a concentration varying between 5 and 0.4 g/kg of flour. Sustain the enzymatically treated solution continuously in the jet cooker at the same rate of flow. Heat the solution at 130° (2 with a pressure of $2 \times 10^5$ Pa by a vapor injection, and maintain for approximately 12 minutes. After removing it from the chamber, cool the solution to 95° C. by a shock effect and let flow in a reactor. Centrifuge the solution at 90° C. in a horizontal decanter allowing the insoluble part to separate.

The centrifuged part can be dried on a heated, vaporized rolling drier. The flaked product is then crushed and/or granulated, if the case arises, in a multiple effect atomizer.

Table VIII shows the physical-chemical characteristics of water soluble extracts of oat flour obtained from different enzymes, according to the preceding operating procedure.

TABLE VIII

| Experiment No. | Enzymes | quantity g/kg | % proteins | % lipids | % β-glucan | D.E. Dextrose equivalent | viscosity mPa · s | pH |
|---|---|---|---|---|---|---|---|---|
| 1 | cellulase | 0.42 | 7.5 | 0.9 | 3.4 | 1 | 55 | 6.2 |
| 2 | CGTase | 4 | 10.3 | 1.3 | 2.7 | 0.64 | 45 | 6.5 |
| 3 | pullulanase | 4.6 | 10.8 | 1.1 | 2.6 | 0.3 | 68 | 6.5 |
| 4 | protease | 2.6 | 10 | 2.2 | 2 | 0.2 | 76 | 6.3 |
| 5 | amyloglucosidase | 2.0 | 11.2 | 1.3 | 2.8 | 2.8 | 46 | 6.5 |
| 6 | α-amylase | 0.29 | 8.5 | 3.0 | 3.5 | 0.2 | 58 | 6.3 |

EXAMPLE 8

Effect of the enzyme content.

Sample 5, shown in table VIII, was reproduced for different concentrations of amyloglucosidase while maintaining the same operating conditions as explained in Example 7. The effect of this parameter was noted vis-a-vis the viscosity developed by the end product and returned to a 5% solution in water.

The corresponding results are shown below in Table IX.

TABLE IX

| Quantity g/kg | 2.0 | 2.8 | 5 |
|---|---|---|---|
| viscosity mPa·s | 26 | 30 | 8 |
| D.E. Dextrose equivalent | 2.8 | 12 | 23 |

The results show that there is an optimal quantity of enzymes to obtain the anticipated product. Thus, water soluble or water dispersible extracts having a given viscosity or degree of hydrolysis can be prepared, by means of the preparation process of this invention.

It is understood that the foregoing description is given merely by way of illustration and that modification and variations may be made therein without departing from the spirit and scope of the invention:

What is claimed is:

1. A cereal hydrolysate containing composition for use as a fat mimic in foods comprising:
   A. a cereal hydrolysate comprising water soluble dietary fiber material prepared by lydrolyzing an aqueous dispersion of a cereal substrate with an enzyme under conditions which will hydrolyze substrate starch without appreciable solubilization of substrate protein to yield water soluble and insoluble fractions, the water soluble dietary fiber material being isolated from the water soluble fraction, and
   B. a hydrocolloid gum effective and in an amount sufficient to form a thermo-irreversible gel with the water soluble dietary fiber material.

2. A composition as recited in claim 1 wherein the enzyme is α-amylase.

3. A composition as recited in claim 1 wherein the enzyme is selected from the group consisting of amyloglucosidases, cellulases, pullulanases, cyclodextrine glycosyltransferase, proteases and mixtures thereof.

4. A composition as recited in claim 3 wherein said enzyme is a cellulase.

5. A composition as recited in claim 1 wherein said cereal substrate dispersion comprises about 10–40% solids.

6. A composition as recited in claim 1 wherein said cereal substrate comprises a flour selected from the group of oats, barley, wheat, corn, rice, rye, triticale and milo from barley.

7. A composition as recited in claim 1 wherein said cereal substrate is oat flour or barley flour.

8. A composition as recited in claim 1 wherein the enzyme and the cereal substrate are gelatinized concurrently with the hydrolysis by treating the substrate with the enzyme at a temperature in the range of about 70°–100° C.

9. A composition as recited as in claim 1 wherein the water soluble fraction is separated from the water insoluble fraction by centrifugation at a temperature less than about 70° C.

10. A composition as recited in claim 1 wherein the cereal hydrolysate is used in proportion to the hydrocolloid gum in a range from about 80 to about 88 parts cereal hydrolysate to about 20 to about 12 parts hydrocolloid gum.

11. A composition is recited in claim 10 wherein the cereal hydrolysate is used in proportion to the hydrocolloid gum in a range from about 83 to about 85 parts cereal hydrolysate to about 17 to about 15 parts hydrocolloid gum.

12. A composition as recited in claim 1 wherein the hydrocolloid is a selected from the group consisting of carrageenan and a mixture of xanthan gum and locust bean gum.

13. A composition as recited in claim 12 wherein the hydrocolloid is k-carrageenan or i-carrageenan.

14. A food composition containing a fat mimic comprising
   A. a cereal hydrolysate prepared by hydrolyzing an aqueous dispersion or a cereal substrate with an enzyme selected from the group consisting of amylases, amyloglucosidases, cellulases, pullulanases, cyclodextrine glycosyltransferase, proteases and mixtures thereof under conditions which will hydrolyze substrate starch without appreciable solubilization of substrate protein to yield water soluble and insoluble fractions, the cereal hydrolysate being selected from the group consisting of a) the water soluble fraction,
   b) the water insoluble fraction, c) water soluble dietary fiber solids isolated from the water soluble fraction and d) a combination of a) and b),
   B. a hydrocolloid gum effective and in an amount sufficient to provide texture and mouth feel comparable to a full fat product, and
   C. a meat component.

15. A composition as recited in claim 14 wherein the cereal hydrolysate contains the water soluble dietary fiber and the hydrocolloid is effective and in an amount sufficient to form a thermo-irreversible gel with the water soluble dietary fiber.

16. A food composition a recited in claim 14 wherein the cereal hydrolysate is used in proportion to the hydrocolloid gum in a range from about 80 to about 88 parts cereal hydrolysate to about 20 to about 12 parts hydrocolloid gum.

17. A food composition as recited in claim 14 wherein the enzyme is a cellulase.

18. A food composition as recited in claim 14 wherein the cereal substrate comprises a flour selected from the group of oats, barley, wheat, corn, rice, rye, triticale, and milo.

19. A food composition as recited in claim 14 wherein the cereal substrate is oat flour, oat bran or barley flour.

20. A food composition as recited in claim 14 wherein the meat is derived from bovines, sheep, swine and fowl.

21. A food composition as recited in claim 14 wherein the meat is sausage.

22. A food composition as recited in claim 14 wherein the hydrocolloid is selected from the group consisting of carrageenan and a mixture of xanthan gum and locust bean gum.

23. A food composition as recited in claim 22 wherein the hydrocolloid is k-carrageenan or i-carrageenan.

24. A food composition a recited in claim 14 wherein the cereal hydrolysate is used in proportion to the hydrocolloid gum in a range from about 80 to about 88 parts cereal hydrolysate to about 20 to about 12 parts hydrocolloid gum.

25. A food composition a recited in claim 24 wherein the cereal hydrolysate is used in proportion to the hydrocolloid gum in a range from about 83 to about 85 parts cereal hydrolysate to about 17 to about 15 parts hydrocolloid gum.

26. A composition as recited in claim 14 wherein the enzyme is a cellulase.

27. A food composition comprising a dietary fiber product produced by the method of:

a. treating an aqueous dispersion of a cereal substrate with an enzyme selected from the group consisting of amylases, amyloglucosidases, cellulases, pullulanases, cyclodextrine glycosyltransferase, proteases and mixtures thereof under conditions which will hydrolyze substrate starch without appreciable solubilization of substrate protein and thereby yield a soluble fraction and an insoluble fraction;

b. separating the soluble fraction from the insoluble fraction under conditions which minimize the level of protein in the soluble fraction;

c. recovering from the soluble fraction, water soluble dietary fiber substantially free of water insoluble fiber; and d. combining the water soluble dietary fiber with a hydrocolloid and meat component.

28. A food composition as recited in claim 27 wherein the hydrocolloid is effective and in an amount sufficient to form a thermo-irreversible gel with said water soluble dietary fiber.

29. A cereal hydrolysate containing composition for use as a fat mimic in foods comprising:

A. a cereal hydrolysate composition prepared by hydrolyzing an aqueous dispersion of a cereal substrate with an enzyme under conditions which will hydrolyse substrate starch without appreciable solubilization of substrate protein to yield a water soluble and insoluble fractions, the cereal hydrolysate composition selected from the group consisting of a) the water soluble fraction, b) the water insoluble fraction, c) water soluble dietary fiber solids isolated from the water soluble fraction and d) a combination of a) and b), and B. a hydrocolloid gum effective and in an amount sufficient to provide a fat reduced product having the texture and mouth feel comparable to a full fat product.

30. A composition as recited in claim 29 wherein the enzyme is α-amylase.

31. A food composition containing a tat mimic comprising

A. a cereal hydrolysate composition prepared by hydrolyzing an aqueous dispersion of a cereal substrate with an enzyme under conditions which will hydrolyse the starch without appreciable solubilization of the substrate protein to yield water soluble and insoluble fractions, the cereal hydrosylate composition selected from the group consisting of a) the water soluble fraction, b) the water insoluble fraction, c) water soluble dietary fiber solids isolated from the soluble fraction and d) a combination of a) and b), B. a hydrocolloid gum effective and in an amount sufficient to provide the texture and mouth feel comparable to a full fat product, and C. one or more digestible food components.

32. A food composition as recited in claim 31 wherein the enzyme is α-amylase.

33. A food composition as recited in claim 31 wherein the cereal hydrolysate contains the water soluble dietary fiber and the hydrocolloid is effective and in an amount sufficient to form a thermo-irreversible gel with the water soluble dietary fiber.

34. A food composition comprising a dietary fiber product produced by the method of:

a. treating an aqueous dispersion of a cereal substrate with an enzyme under conditions which will hydrolyze substrate starch without appreciable solubilization of substrate protein and thereby yield a soluble fraction and an insoluble fraction;

b. separating the soluble fraction from the insoluble fraction under conditions which minimize the level of protein in the soluble fraction;

c. recovering from the soluble fraction the water soluble dietary fiber substantially free of water insoluble fiber; and d. combining the water soluble dietary fiber with a hydrocolloid and one or more digestible food components.

35. A food composition as recited in claim 34 wherein the enzyme is α-amylase.

36. A food composition as recited in claim 34 wherein the fiber is combined with the hydrocolloid effective and in an amount sufficient to form a thermo-irreversible gel with the fiber.

37. A food composition as recited in claim 14 wherein the meat component is selected from the group consisting of cooked sausage and fermented sausage.

38. A food composition as recited in claim 14 wherein the enzyme is amylase and the meat component is selected from the group consisting of cooked sausage and fermented sausage.

39. A food composition as recited in claim 14 wherein the meat component is selected from the group consisting of frankfurters, pepperoni, kielbasa, pork sausage, salami and meat loaf.

40. A food composition as recited in claim 14 wherein the enzyme is α-amylase and the meat component is selected from the group consisting of frankfurters, pepperoni, kielbasa, pork sausage, salami and meat loaf.

41. A food composition as recited in claim 40 wherein the meat component is frankfurters.

42. A food composition as recited in claim 40 wherein the meat component is pepperoni.

43. A food composition as recited in claim 42 wherein the pepperoni is on a pizza.

44. A food composition as recited in claim 40 wherein the meat component is kielbasa.

45. A food composition as recited in claim 15 wherein the meat component is selected from the group consisting of cooked sausage and fermented sausage.

46. A food composition as recited in claim 15 wherein the enzyme is α-amylase and the meat component is selected from the group consisting of cooked sausage and fermented sausage.

47. A food composition as recited in claim 15 wherein the enzyme is α-amylase and the meat component is selected from the group consisting of frankfurters, pepperoni, kielbasa, pork sausage, salami and meat loaf.

48. A food composition as recited in claim 47 wherein the meat component is pepperoni.

49. A food composition as recited in claim 47 wherein the meat component is kielbasa.

50. A food composition as recited in claim 47 wherein the meat component is salami.

51. A food composition as recited in claim 27 wherein the meat component is selected from the group consisting of frankfurters, pepperoni, kielbasa, pork sausage, salami and meat loaf.

52. A food composition as recited in claim 27 wherein the enzyme is α-amylase and the meat component is selected from the group consisting of frankfurters, pepperoni, kielbasa, pork sausage, salami and meat loaf.

53. A food composition as recited in claim 53 wherein the meat component is frankfurters.

54. A food composition as recited in claim 53 wherein the meat component is pepperoni.

55. A food composition as recited in claim 53 wherein the meat component is kielbasa.

* * * * *